(12) United States Patent
Hochman (10) Patent No.: US 10,220,180 B2
(45) Date of Patent: Mar. 5, 2019

(54) METHOD AND APPARATUS FOR PERFORMING A PERIPHERAL NERVE BLOCK

(71) Applicant: Mark N. Hochman, New York, NY (US)

(72) Inventor: Mark N. Hochman, New York, NY (US)

(73) Assignee: MILESTONE SCIENTIFIC, INC., Livingston, NJ (US)

( * ) Notice: Subject to any disclaimer, the term of this patent is extended or adjusted under 35 U.S.C. 154(b) by 0 days.

(21) Appl. No.: 15/141,231

(22) Filed: Apr. 28, 2016

(65) Prior Publication Data

US 2017/0106163 A1   Apr. 20, 2017

Related U.S. Application Data

(63) Continuation-in-part of application No. 15/062,685, filed on Mar. 7, 2016, now abandoned.
(Continued)

(51) Int. Cl.
*A61M 1/00* (2006.01)
*A61M 19/00* (2006.01)
(Continued)

(52) U.S. Cl.
CPC .......... *A61M 19/00* (2013.01); *A61B 5/4896* (2013.01); *A61M 5/16854* (2013.01); *A61M 5/20* (2013.01); *A61M 5/427* (2013.01); *A61M 5/5086* (2013.01); *A61N 1/0502* (2013.01); *A61N 1/0551* (2013.01); *A61N 1/3605* (2013.01); *A61N 1/36017* (2013.01); *A61B 2090/0807* (2016.02); *A61B 2090/366* (2016.02); *A61M 2005/1726* (2013.01);
(Continued)

(58) Field of Classification Search
CPC ............................... A61M 5/20; A61M 5/427
USPC .......................................................... 607/46
See application file for complete search history.

(56) References Cited

U.S. PATENT DOCUMENTS 6,159,161 A   12/2000  Hodosh
6,200,289 B1   3/2001  Hochman et al.
(Continued)

OTHER PUBLICATIONS

Gadsden et al., "Opening Injection Pressure Consistently Detects Needle-Nerve Contact during Ultrasound-guided Interscalene Brachial Plexus Block" Anesthesiology, vol. 120, No. 5, May 2014, pp. 1246-1253.
(Continued)

*Primary Examiner* — Nadia A Mahmood
(74) *Attorney, Agent, or Firm* — Stephen H. Eland; Dann, Dorfman, Herrell & Skillman (57) ABSTRACT

A system for infusing medication into a mammalian subject is provided. The system includes an injection system for controlling a flow of fluid from a fluid reservoir to a needle. A sensor is provided that detects a characteristic indicative of the fluid pressure in the needle. The injection system controls the flow of fluid to the needle in response to the characteristic detected by the sensor and the sensor continuously detects the characteristic as the needle is inserted into the subject. The system further includes a conductive element for providing electric nerve stimulation, wherein the system provides electric nerve stimulation in response to the sensor detecting a pressure exceeding an upper limit.

20 Claims, 4 Drawing Sheets

Related U.S. Application Data (60) Provisional application No. 62/242,745, filed on Oct. 16, 2015.

(51) Int. Cl.

| | | |
|---|---|---|
| *A61M 5/20* | (2006.01) | |
| *A61M 5/42* | (2006.01) | |
| *A61M 5/50* | (2006.01) | |
| *A61N 1/05* | (2006.01) | |
| *A61M 5/168* | (2006.01) | |
| *A61B 5/00* | (2006.01) | |
| *A61N 1/36* | (2006.01) | |
| *A61M 5/172* | (2006.01) | |
| *A61B 90/00* | (2016.01) | |

(52) U.S. Cl.
CPC . *A61M 2205/13* (2013.01); *A61M 2205/3344* (2013.01); *A61M 2205/52* (2013.01); *A61M 2205/581* (2013.01); *A61M 2205/582* (2013.01); *A61M 2205/583* (2013.01); *A61M 2205/587* (2013.01); *A61M 2210/1003* (2013.01); *A61M 2230/60* (2013.01); *A61N 1/36031* (2017.08)

(56) References Cited

U.S. PATENT DOCUMENTS

| | | |
|---|---|---|
| 6,652,482 B2 | 11/2003 | Hochman |
| 6,786,885 B2 | 9/2004 | Hochman et al. |
| 6,886,648 B1 | 3/2005 | Hadzic et al. |
| 6,887,216 B2 | 5/2005 | Hochman et al. |
| 7,449,008 B2 | 11/2008 | Hochman |
| 7,618,409 B2 | 11/2009 | Hochman |
| 7,896,833 B2 | 3/2011 | Hochman |
| 2004/0035743 A1 | 2/2004 | Tighe |
| 2004/0149282 A1 | 8/2004 | Hickle |
| 2006/0122555 A1 | 6/2006 | Hochman |
| 2008/0058702 A1 | 3/2008 | Arndt et al. |
| 2009/0149911 A1 | 6/2009 | Dacey, Jr. et al. |
| 2009/0149912 A1 | 6/2009 | Dacey, Jr. et al. |
| 2009/0210029 A1 | 8/2009 | Tsui |
| 2010/0049270 A1* | 2/2010 | Pastore .............. A61N 1/3627 607/22 |
| 2010/0274191 A1 | 10/2010 | Ting |
| 2011/0112511 A1 | 5/2011 | Singer |
| 2011/0190596 A1 | 8/2011 | Hacker |
| 2012/0022407 A1 | 1/2012 | Lechner |
| 2012/0232389 A1 | 9/2012 | Guzman |
| 2012/0289819 A1 | 11/2012 | Snow |
| 2013/0053851 A1 | 2/2013 | Schmitz et al. |
| 2013/0261533 A1 | 10/2013 | Norkunas |
| 2014/0012226 A1 | 1/2014 | Hochman |
| 2014/0207050 A1 | 7/2014 | Gonzalez et al. |
| 2014/0221965 A1 | 8/2014 | Regittnig |
| 2014/0316268 A1 | 10/2014 | Kafiluddi et al. |
| 2014/0343406 A1 | 11/2014 | Damjanovic |
| 2015/0283365 A1 | 10/2015 | Dacey, Jr. et al. |

OTHER PUBLICATIONS

Cohen et al., "Functional deficits after intraneural injection during interscalene block", Regional Anesthesia and Pain Medicine, vol. 35, No. 4, Jul.-Aug. 2010, pp. 397-399.

Reiss et al., "Nerve injury complicating ultrasound/electrostimulation-guided supraclavicular brachial plexus block", Regional Anesthesia and Pain Medicine, vol. 35, No. 4, Jul.-Aug. 2010, pp. 400-401.

Lupu et al., "Nerve expansion seen on ultrasound predicts histologic but not functional nerve injury after intraneural injection in pigs", Regional Anesthesia and Pain Medicine, vol. 35, No. 2, Mar.-Apr. 2010, pp. 132-139.

Steinfeldt et al., "Histological consequences of needle-nerve contact following nerve stimulation in a pig model", Anesthesiology Research and Practice, vol. 2011, Feb. 2011, 9 pages.

Steinfeldt et al., "Forced needle advancement during needle-nerve contact in a porcine model: Histological outcome", Anesthesia & Analgesia, vol. 113, No. 2, Aug. 2011, pp. 417-420.

Sites et al., "Characterizing novice behavior associated with learning ultrasound-guided peripheral regional anesthesia", Regional Anesthesia and Pain Medicine, vol. 32, No. 2, Mar.-Apr. 2007, pp. 107-115.

Sites et al., "Incidence of local anesthetic systemic toxicity and postoperative neurologic symptoms associated with 12,668 ultrasound-guided nerve blocks", Regional Anesthesia and Pain Medicine, vol. 37, No. 5, Sep.-Oct. 2012, pp. 478-482.

Liu et al., "Incidence of unintentional intraneural injection and postoperative neurological complications with ultrasound-juided interscalene and supraclavicular nerve blocks", Anaesthesia vol. 66, 2011, pp. 168-174.

Abstract of: Bilbao et al., "Neurological complications associated with ultrasound-guided interscalene and supraclavicular block in elective surgery of the shoulder and arm. Prospective observational study in a university hospital", Rev Esp Anestesiol Reanim, vol. 60, No. 7, Aug.-Sep. 2013, pp. 384-391.

Widmer et al., "Incidence and severity of complications due to femoral nerve blocks performed for knee surgery", The Knee, Nov. 2012, 5 pages.

Hadzic et al., "Combination of intraneural injection and high injection pressure leads to fascicular injury and neurologic deficits in dogs", Regional Anesthesia and Pain Medicine, vol. 29 No. 5 Sep.-Oct. 2004, pp. 417-423.

Kapur et al., "Neurologic and histologic outcome after intraneural injections of lidocaine in canine sciatic nerves", ACTA, Anaesthesiologica Scandinavica, vol. 51, 2007, pp. 101-107.

International Search Report issued in International Patent Application No. PCT/US16/57264 dated Mar. 22, 2017.

International Preliminary Report on Patentability issued in International Patent Application No. PCT/US16/57264 dated Apr. 17, 2018.

\* cited by examiner

METHOD AND APPARATUS FOR PERFORMING A PERIPHERAL NERVE BLOCK

PRIORITY APPLICATIONS

The present application is a continuation-in-part of U.S. patent application Ser. No. 15/062,685 filed on Mar. 7, 2016. The entire disclosure of the foregoing patent application is hereby incorporated herein by reference. This application also claims priority to U.S. Provisional Patent Application No. 62/242,745 filed Oct. 16, 2015.

FIELD OF THE INVENTION

The present invention relates generally to improvements to the delivery of drugs, particularly to systems for subcutaneous injection/aspiration into the body. More specifically, the invention provides a method and apparatus for distinguishing between different tissue types when performing a Peripheral Nerve Block.

BACKGROUND OF THE INVENTION

A peripheral nerve block (PNB) is used for anesthesia, postoperative analgesia, and diagnosis and treatment of chronic pain syndromes. Peripheral nerve blocks may also improve acute pain management and patient disposition even when used only as adjunct techniques. An objective of the PNB regional anesthesia technique is to identify the target nerve and position a hollow-bore needle in a defined proximity relative to the targeted nerve without causing untoward reactions such as structure damage to the nerve or causing excessive pain to the patient.

The current state-of-the-art for performing the PNB technique relies upon an adjunctive technology such as ultrasound to determine the general location of the needle relative to the position of the nerve and vascular components surrounding the nerve. Approximately 80% of PNB procedures performed utilize ultrasound as a primary means of locating the nerve. In fact, the medical literature currently advocates using ultrasound and notes that nerve stimulation is non-specific and unreliable.

Figure 1:
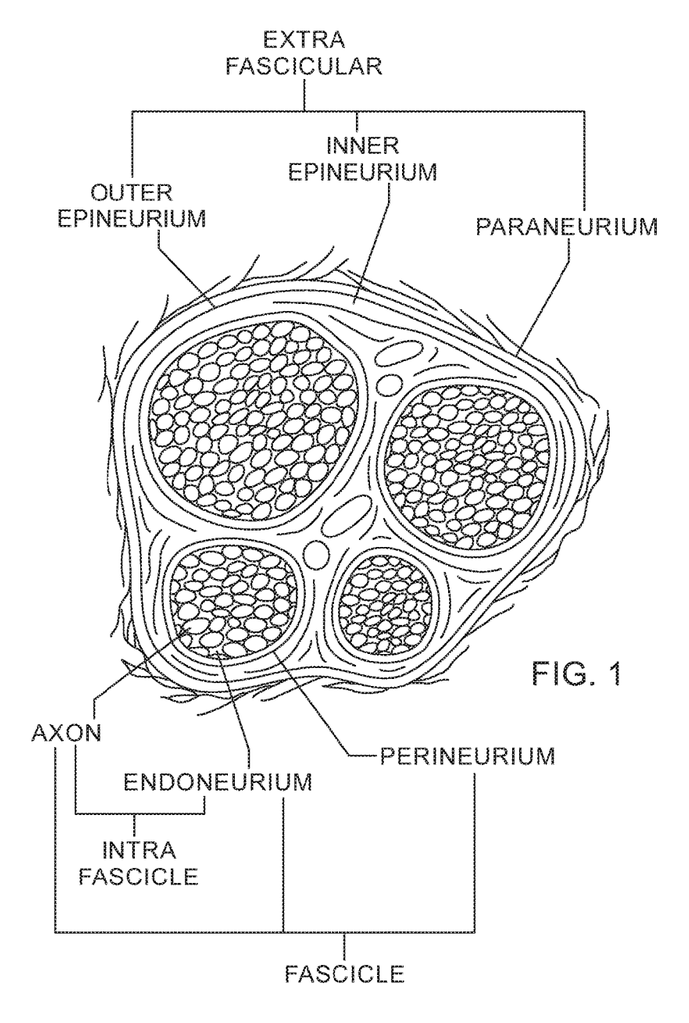
FIG. 1 is a cross-section view of a fascicle of nerve fibers.

Referring to FIG. 1, a description of the microanatomy of the peripheral nervous system is provided. The basic building block to both the central and peripheral nervous system is the single cell unit commonly known as is the axon. The brain and central nervous system are composed of millions of axons. Branching off the central nervous system of the brain stem and spinal cord is a collection of highly organized axons forming a network of sensory and motor pathways via the axons. This network of pathways is collectively known as the peripheral nervous system.

In the peripheral nervous system, each individual axon is surrounded by supporting connective tissue called the endoneurium. Contained within the endoneurium are small blood vessels (capillaries and venuoles) providing nutrients to these axons. Axons are collectively formed into highly organized, packed bundles that are surrounded by a thin but dense multi-layered connective tissue sheath that surrounds and forms a membrane structure called the perineurium. The perineurium provides a dense protective layer that is both a physical and chemical barrier, providing a degree of protection for the axons and endoneurium. This barrier is akin to the blood-brain barrier.

This discrete unit of the endoneurium and perineurium is called a peripheral nerve fascicle. When fascicles coalesce together they form fascicular bundles embedded in epineurium, which is a connective tissue sometimes referred to as inner epineurium. The multiple groups of fascicles are embedded in a non-uniform matrix of connective tissue (fibro-adipose tissue) and mid-size vessels that are loosely arranged together with an outer perimeter of dense connective tissue. The bundled fascicular structures collectively surrounded by this additional densely, more highly organized layer of fibrous tissue, houses the peripheral nerve contents and is known as the outer epineurium.

The outer epineurium connects the outer layer to the neighboring structures. A loose connective tissue fills the space between the nerve and the surrounding tissue in connection with the outer epineurium. There is thus an additional multi-layer boundary beyond the outer epineurium that runs along the entire trajectory of the nerve and is composed of an extraneural connective tissue known as the paraneurium. The paraneurium is a distinct multi-layer functional structure that enables the nerve to glide relative to other anatomic structures during muscular-skeletal movements.

To aid in locating a nerve branch, electrical stimulation was proposed in the year 1912. Electrical nerve stimulation was introduced from an understanding that nerve transmission is an electro-chemical response of excitation along the nerve (an axon). Introducing an electrical current stimulation to the body had the ability to elicit an indirect excitation of both the sensory and motor components of a nerve. This was found to provide a visual muscle contraction when the electrical stimulation was applied. Modulating the charge frequency and intensity lead to contraction and relaxation of muscle groups innervated by a nerve branch. This use of an indirect electrical charge to produce a nerve reaction to a specific nerve did not gain popularity because clinicians were unable to precisely control the various parameters of the current applied. The same deficiencies known when nerve stimulation was first introduced still exist today, including:

An inability to accurately modulate an applied electrical charge at a given distances to the surface of a nerve branch has made nerve stimulation limited in the identification of a specific nerve branch when using nerve stimulation as the primary means of nerve branch location. A variety of charge intensities are recommended at specific distances when approaching the nerve branch blindly ranging from an intensity of 2.0 mA to 0.2 mA. However, distance and intensity noted by a visual muscle twitch reaction does not correlate. Therefore, a reaction to a greater stimulation does not necessarily mean the needle is a greater distance to the intended nerve branch. And a reaction to a lower electric charge does not mean the needle is closer to the surface extraneural position and/or located within the nerve, i.e., achieved an intraneural location. In fact, there appears to be no consensus on the location of a needle (intraneural or extraneural) based on a reaction to an applied electrical charge irrespective of the intensity, frequency and duration applied to the nerve at a given distance.

A further deficiency of nerve stimulation technique is the inability to set the appropriate charge for a defined distance from the outer surface of the fascicle, i.e., Extra-Fascicular. It is more concerning if a high charge above 1.0 mA is utilized Intra-Fascicular, as it may cause a severe response by the patient or, even worse, result in irreversible damage from an excessive electrical charge applied directly on the axon. Hence there is an inability to determine what appropriate charge should be applied for a specific distance from the fascicle.

A further deficiency is that confounding variables make the use of nerve stimulation a non-specific technique. These are related to anatomic variations within a given patient as well as anatomic variation between different patients. The body is comprised of a variety of tissue types which include connective tissue of mineralized and non-mineralized tissues. These tissues are composed of water and collagen, adipose tissue (fat), muscle, fluids (blood), bone, cartilage, etc. Each of these tissues types provides a different resistance and/or capacitance to a charge when it is applied at a given distance to the intended target. The variables of tissue cannot be underestimated or anticipated. Hence current devices lack the ability to quantify a specific charge to a specific location. This has lead to an inability to produce predictable response to a given electrical charge when used as the primary means of determining location or proximity to a specific nerve.

In summary, the variables of charge intensity, frequency and tissue resistance to the electric charge have made it difficult to standardize a technique to enable location of a specific nerve branch.

SUMMARY OF THE INVENTION

In view of the shortcomings of the prior art, one aspect of the present invention provides a mechanism for distinguishing between intra-fascicular and extra-fascicular needle placement.

Another aspect of the current invention is a current charge that is transmitted via an ionic solution through a disposable syringe and tubing to the tip of the needle for the purpose of nerve stimulation.

A further aspect of the current invention is a system that provides a constant flow of fluid from the tip of the needle during the advancement of a needle movement through tissues when performing a peripheral nerve block to prevent the needle tip from entering the fascicle. The constant flow of fluid from a needle tip acts as a means to move or push dense structures away from the tip of a needle as it advances.

Yet another aspect of the current invention is a system that provides a defined rate or pace of forward movement to the needle within the tissues to prevent a biasing counter head-pressure force applied upon a needle as one is advancing said needle into and through the tissues while simultaneously and continuously measuring a pressure at tip of the needle.

Still another aspect of the current invention provides that when the needle is not being advanced the counter head-pressure will not be subtracted from the calculation of the exit-pressure. It is understood that the button or control on the hand-piece may also be activated to correspond with the forward movements in which the counter head-pressure is subtracted from the calculation of the head-pressure therefore providing a means to distinguish between when the needle is being advanced and when the needle remains stationary within the tissues.

The current invention also provides a hand-piece to which a marked needle is connected that is designed to house a small LED light or display screen and/or speaker that will blinks and/or beep in coordination to said rate to advance said needle. The hand-piece may possess input elements to control flow-rate, electrical current stimulation and communicate with the CPU of the drive unit. Additionally, the hand-piece may possess a vibratory chip or element to provide vibration of the hand-piece to communicate a command or signal from the CPU to the operator. This vibratory sensation can be discreet and represent a command warning or signal for the operator to respond to. The hand-piece may also include an output display to additional display information.

The present invention also provides an injection device for providing a peripheral nerve block that uses maximum back pressure range between 75 mm/Hg to 500 mm/Hg to trigger an electrical stimulation. An instantaneous discrete emission of a current may be provided when a specific pressure value is detected within the pressure range. This signal is to control an instantaneous discreet emission of a current at a specific pressure value within stated pressure range.

According to another aspect, the system uses a biasing head-pressure value that is set in a CPU that is determined and correlated to a rate (pace) of forward movement to the marked needle within the tissues. Biasing head-pressure value is calculated and is factored into the calculated head pressure value to eliminate pressure bias from the counter head-pressure value of a needle resulting from forward movement during simultaneously use of continuous flow and pressure monitoring.

According to a further aspect, an injection device is provided that provides a current between 0.15 mA to 2.0 mA. The current is provided in response to a detected exit-pressure value. Further, the electric charge is to be emitted as for a discreet period between 1.0 to 10.0 seconds. Simultaneously, when the electric charge is emitted a control signal is transmitted to the CPU to which a response is required. An example of a response to the control signal would be:
  i) verification of muscle twitch.
  ii) change to higher flow-rate to dispense drug.

A further aspect of the present invention is to have a first condition (specific exit-pressure value at a fixed-flow rate) and second condition (emitted current stimulation) requiring a response by the operator to set a third condition (positive/negative observation) to result in an output (instruction and warning signal).

Yet another aspect of the present invention is a device that provides a means to advance the needle within the tissues at an advancement rate between 2 and 20 mm/sec with constant flow of fluid at a defined flow-rate.

According to a still further aspect, the present invention provides a method and apparatus for utilizing counter-head pressure when calculating the exit pressure. The counter-head pressure is related to the insertion rate of the needle. Therefore, the system includes a mechanism for controlling the insertion rate of the needle. In particular, the system may include markings on the needle and auditory or visual cues for prompting the appropriate insertion rate for the needle.

Additionally, another aspect of the present invention provides a hand-piece to which a marked needle is connected that is designed to house a small display, such as an LED light or display screen that will provide a blink or visual instruction and/or speaker and/or beeps or provides an audible tone that can be intermittent to enable the coordination of the defined forward movement to the provided visual or audible signal to the advancement of the needle based upon the markers on the surface of the needle as it penetrates the skin or other part of the body. The audible and visual cadence defines the rate of advancement of the needle so that it can be coordinated to forward movement to improve the accuracy of counter head-pressure produced and provided to the calculation of the real-time exit-pressure monitoring.

BRIEF DESCRIPTION OF THE DRAWINGS

The foregoing summary and the following detailed description of the preferred embodiments of the present invention will be best understood when read in conjunction with the appended drawings, in which.

DETAILED DESCRIPTION OF THE INVENTION

Figure 2:
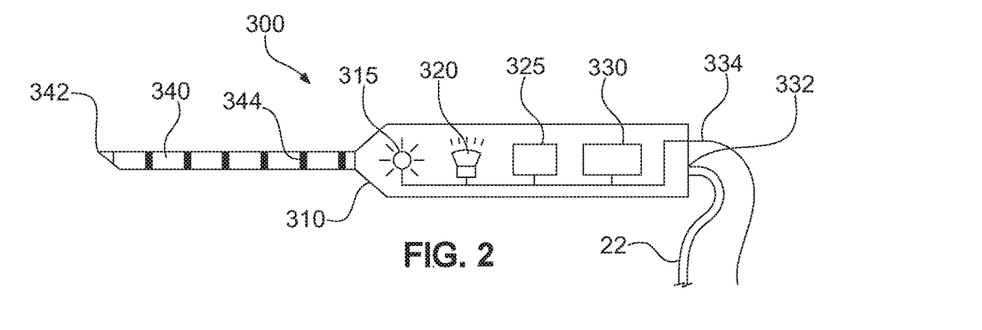
FIG. 2 is a diagrammatic view of drug delivery system.
Figure 3:
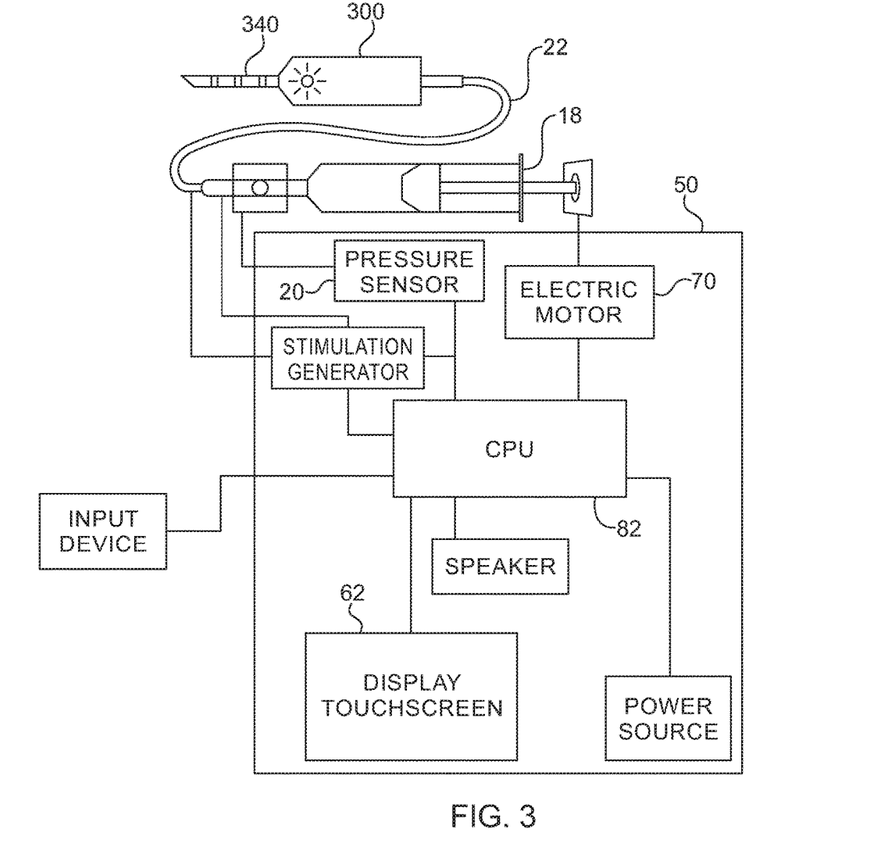
FIG. 3 is side view of an injection device of the drug delivery system illustrated in FIG. 2.

Referring now to the drawings, in general and to FIGS. 1-3 specifically, a drug infusion system is designated generally 5. The system 5 includes an injection assembly 10 and a computer-controlled drug delivery instrument 50, referred to as a drive unit. The injection assembly 10 includes an insertion needle 340 configured for insertion into a mammalian subject. The injection assembly 10 is connected with the drive unit 50, which controls the flow of fluid to the injection assembly during use. The system 5 also includes one or more output mechanisms that provide data to the medical professional during a procedure to assist in proper placement of the needle in the subject.

The system 5 is operable to determine the location for an intra-fascicular needle location. The system is also operable to deliver therapeutic medication to an intra-fascicular needle location. The medication may include, but is not limited to local anesthetic solutions, such as, cortico-steroids, hydroxyapatite, joint replenishment drugs, sclerosing agents and other drugs that are typically injected into a fluid-filled tissue space for therapeutic purposes.

An intra-fascicular needle location is one in which the tip of the needle penetrates through the perineurium so that the needle tip is located inside the fascicle. An extra-fascicular needle location is a position in which the needle is anywhere outside the perineurium of an individual fascicle, which may include outside the outer epineurium or even the paraneurium thereby defined as completely extraneural.

Irreversible damage can occur to a nerve when the needle tip is both embedded into a fascicle and then fluid under hydrostatic pressure produces changes to the neural and vascular tissues within the fascicle. This occurs because the outer layer of the fascicle is a protective layer of a relatively non-compliant, rigid protective structure. This protects the basic components of the nerve, the axons, which are densely packed within the fascicle. In other words, the fascicle represents a densely packed arrangement with a thick protective shell. The fascicle does not readily deform by either expanding or contracting. Therefore, tissue compliance to an inflow of fluids is extremely low and/or non-existent. Needle penetration into the fascicule may not necessarily cause the ultimate damage to the axon units, but the combined effect of needle penetration and increased pressure inside the fascicle from the infusion of fluids inside the fascicle can produce damage to the capillary bed. Additionally, fluid pressure-induced strangulation of the microcirculation of the axons impedes short-term nutrient replenishment after such physical trauma thus leading to initial necrosis. The cascade from necrosis leads to an inflammatory response in an effort to initiate a wound healing from the initial pressure-induced trauma further advancing or cascading potentially toward irreversible damage.

However, there are instances in which intentional intra-fascicular needle placement is desirable and required. Such instances include unresolved phantom pain after a limb is removed. Additionally, hyperactive neural stimulation of a particular limb may sometimes lead to retractable pain and is another circumstance in which intentional intra-fascicular needle location and delivery of agents is required. Accordingly, the system 5 and its use provide a method and apparatus for effectively discriminating between the extra-fascicular and intra-fascicular location of a needle.

Injected fluid disperses through tissue at different rates. As a result, the fluid pressure varies. Therefore, this fluid pressure (or an internal pressure related to the resistance pressure of a tissue) is indicative of, and may be used to identify several types of tissues.

The system 5 enables a practitioner to accurately identify fluid-filled tissue space while limiting the placement of drugs into non-targeted tissues. This is performed for both diagnostic and therapeutic procedures. The system 5 utilizes the pressure of a fluid from a needle or catheter following placement of the needle/catheter within the tissue in order to identify the accuracy of placement and to monitor the placement during an injection or aspiration.

Specifically, the system 5 includes one or more output mechanisms for providing audible and/or visual feedback of the detected fluid pressure in the insertion needle. The operator uses the visual feedback as guidance during the placement of the insertion needle. As shown in FIGS. 2&3, the first output mechanism may be a video display screen, such as an LCD display for displaying data to aid the operator. Additionally, a second output mechanism may also be provided. For example, the second output mechanism may be a speaker for providing an output signal.

Injection Assembly

Referring to FIGS. 2-3, the system 5 includes a injection assembly 10 that includes a syringe 18 and an elongated length of flexible tubing 22 having a first end connected with the syringe and an insertion needle 340 connected with the second end. In this way, fluid from the syringe can be expelled through the tubing 22 and into the needle 24. The injection assembly 10 also includes a pressure sensor for detecting fluid pressure in the injection assembly. The pressure sensor may be disposed in one of several locations to measure a pressure that correlates with the fluid pressure at the tip of the needle 340. In the present instance, the pressure sensor 20 is an inline fluid pressure sensor attached to the syringe 18 between the syringe and the tubing 22. In this way, the pressure sensor 20 senses the fluid pressure as the fluid exits the syringe and enters the tubing 22 to which the insertion needle 340 is connected.

The injection system 10 may also include a re-useable hand-piece 300 to which the needle is attached. As shown in FIG. 2, the insertion needle 340 is connected to the forward end of the hand piece and the tubing 22 is connected to the rearward end of the hand piece. The hand piece 300 may include features that assist the operator during the insertion process, as described further below. Additionally, the hand piece 300 may be configured to provide electrical stimulation as discussed further below.

The injection assembly may be manually operated to inject fluid. However, in the present instance, a computer-controlled drug delivery system 50 controls the flow of fluid from the injection assembly as discussed further below. An output cable 21 connects the pressure sensor 20 with the drug delivery system 50 so that the drug delivery system can monitor and, if desired, vary the flow of fluid from the syringe in response to the data from the pressure sensor 20. The pressure-transducer 20 may be connected inline between the forward end of the cylinder of syringe 18, and the first end of tubing 22. One exemplary connection is a Luer connection for connecting the pressure-transducer 20 to the tip of the syringe. The connection may be fixed by a threaded connection and/or an irreversible threaded connection, such as a LuerLok. Alternatively, the pressure transducer 20 may be permanently fixed to the syringe by plastic welding or chemical binding, such as adhesive. In this way, the instantaneous, actual fluid pressure in the drug delivery line 22 is sensed and used by the instrument, thereby providing a close approximation to the actual, instantaneous fluid pressure at the point or tip of the needle 340, and therefore, at the location in the patient's body where the needle tip is located. The electronic pressure-transducer 20 provides pressure data via electronic data cables that are connected directly to the central unit 50 to collect the pressure measurements.

The electronic pressure transducer 20 can be any of various pressure sensors. One type of exemplary sensor is a piezoelectric pressure sensor, such as sensors available from Merit Medical Systems, Inc. such as the Meritrans® Pressure Transducer item MER212.

The preferred embodiment is a bonded disposable setup. It is anticipated that a variety of configurations could be used in conjunction with the instrument 50. These consist of different size components, i.e. syringe, tubing-set and pressure transducers. The system may incorporate an identification connector that uniquely identifies the details of each injection assembly (e.g. tube length etc.) The integration of an identification connector confirms and identifies the disposable set-up to be used. It is anticipated that a pre-filled syringe 18 with a drug could be supplied with the injection assembly 10, or the syringe can be supplied empty so that it can be filled onsite with a desired drug, saline or other fluid. For pre-filled syringes 18, the identification connector may also specify the information related to the drug contained within the syringe.

Automated Fluid Delivery System

As described above, the system 5 may include a fluid delivery system 50 for providing a controlled flow of medication to the injection assembly 10. Preferably the fluid delivery system is an automated system and in the present instance is a computer controlled fluid delivery system referred to as a drive unit 50.

Referring to FIGS. 1-4, the drive unit is designed to work in connection with an injection element, such as syringe 18. The drive unit 50 may include a cradle 52 configured to receive the syringe 18 and a clamp for retaining the syringe in the cradle 52. The drive unit 50 includes a drive element operable to drive the plunger in the syringe to expel fluid from the syringe. The drive unit 50 controls the displacement of the drive element thereby controlling ejection of fluid from the syringe. In the present instance, the drive element may include a motor 70 driving an arm engaging the plunger. Driving the motor in a first direction drives the arm forwardly to advance the plunger, thereby expelling fluid. The CPU 82 of the drive unit provides signals to the motor to control operation of the motor.

The drive unit 50 is operable to provide constant or variable fluid flow. In the present instance, the drive unit may provide a non-continuous fluid flow in response to signals received from the electronic pressure-transducer 20, which continuously senses the pressure of the fluid during an insertion/injection procedure. Based on a pre-determined pressure, the drive unit 50 may stop the flow of fluid when the detected pressure exceeds a pre-defined threshold. The pre-defined threshold may be set by the practitioner and stored in a memory 80 of a microprocessor or computer 82 of the electronics in drive unit 50. Similarly, based on a pre-determined pressure, fluid-flow will resume when the fluid pressure falls below a pre-determined pressure. The same pre-determined pressure may be used to control the stopping and re-starting of the fluid flow. In such case the pressure will build as fluid initially enters the tissue to a pre-determined level and then stop until the pressure drops below this pre-determined level. Once the fluid pressure falls below the pre-determined level, the fluid-flow will resume. In this way, the flow of fluid may start and stop during the procedure creating a non-continuous fluid flow.

The system may include pre-defined pressure thresholds used to control the flow of medication from the syringe 18 during the procedure. This enables a clinician to selectively inject drugs into specific sites and intended tissues for diagnostic and therapeutic procedures. Pre-selected maximum allowable pressure limits and/or flow rates are stored in memory 80 and define either the maximum recommended pressures that patients usually tolerate, or other criteria. As the pressure approaches this limit, a visual and/or audible alarm is generated for the clinician, i.e. on screen 62 and via speaker 84 that is activated by data from the microprocessor 82. In addition, data descriptive of the whole injection process is stored for future analysis in memory 80.

The system 5 may directly measure the fluid pressure in the injection assembly 10 or the system may measure a characteristic indicative of the fluid pressure in the injection assembly. For instance, the pressure may be measured by detecting the pressure resistance measured during infusion. The pressure resistance measured is converted into a visual signal on a continuous basis during the insertion procedure. However, the flow rate of medication during the procedure may be based on the fluid pressure detected in real time during the procedure. Therefore, the flow rate of the medication is variable and is dependent on the pressure in the system. In this way, the fluid pressure may be the primary controlling variable of the system.

The flow-rate, therefore, becomes a secondary variable that is modulated within a pre-determined range in order to maintain the desired fluid-flow. In one specific embodiment, the fluid flow is stopped when the pressure exceeds a pre-determined threshold (maximum pressure). The flow-rate, as a secondary variable, may be limited so that fluid injections are not unduly rapid under low pressure conditions. It is contemplated that the relationship between pressure and fluid flow rate may either be binary or continuous. A binary relationship exists when the injection device is configured to deliver a fluid at a single, pre-determined flow rate for any pressure less than the pre-set maximum. Thus, the fluid flow is either on or off based on whether or not the pressure exceeds the threshold. Alternatively, the flow rate may be modulated as a function of pressure. In this case, flow rate will be reduced as the maximum pressure is approached and increased as the pressure drops. Optionally, the flow rate may be limited to a first pre-set maximum pressure and a flow rate resumes at a second distinct pre-determined pressure.

As mentioned above, the system 5 may include a mechanism for displaying relevant injection data including, for example, instantaneous flow rates, pressures, and injection amounts upon a screen 62 of the drive unit 50. Similarly, the system may include a mechanism for recording such information for subsequent analysis after the procedure is performed. For instance, the system may include a non-volatile electronic storage medium, such as a hard drive, flash drive, optical drive or other medium for storing electronic data.

All measurements and information may be presented to the clinician in "real-time" so that the clinician may determine whether the injection is being delivered to the intended location and/or correct tissues and may modify the injection technique accordingly. In addition, the measurements may be recorded for later review and documentation of the clinical event.

It is also contemplated that multiple syringes driven by separate syringe plungers may be used to allow multiple drugs to be injected as well as a second syringe drive that does not required a pre-determined pressure to be reached for any said purpose. The second drive can be programmed on a specific flow-rate to allow infusion of a drug such as local anesthetic and other therapeutic drugs into a variety of tissues.

In yet another embodiment the device may contain two distinct syringe drives in which both are capable of modulation based on fluid-pressure as previously herein described.

Electrical Stimulation

The system may also include an electrical stimulation element 334 for providing electrical nerve stimuli to a target tissue in a patient. The electrical stimulation element is a conductive element connected with the hand piece 300. The electrical stimulation element is operable to provide an electrical charge of low intensity (i.e. approximately 0.15 mA up to approximately 2.0 mA) and short duration (i.e. pulses of approximately 0.1 to 1 Ms). The electronic stimulation elements provide the stimuli for a short time (i.e. approximately 1-10 seconds).

The electric stimulator may be an external element or an internal element. For example, FIGS. 2-3 illustrate an embodiment that incorporates external electric stimuli. A conductive element 334 such as an electrically conductive cable interconnects the hand piece 300 with a stimuli generator 335, so that electrical stimuli are transmitted to the hand piece from the stimuli generator. In turn, the hand piece is connected with an element configured to deliver the electrical charge to the tissue. For instance, the needle 340 may be formed of electrically conductive material and the hand piece may include a connection with the needle providing an electrical pathway from the conductive element and the needle. Alternatively, a conductive element, such as a wire, may extend along the length of the needle and the needle may be electrically insulated from the needle. For example, the needle may be formed of electrically insulative material. An example of an external electric stimulation element is the insulated needle sold under the trade name "Stimuplex®" or the over the needle catheter sold under the trade name "Contiplex® C" by B. Braun Medical Inc. of Bethlehem, Pa.

Alternatively, the system may utilize internal electric stimuli. For example, the fluid injected from the syringe may be an ionic solution capable of conducting electric stimuli. A conductive element may be interconnected with the fluid within an insulated needle. The needle may be constructed from a variety of non-conductive materials. For instance, the conductive element may project into the fluid path at some point between the syringe 18 and the needle 340. For example, the conductive element may impart the electric stimuli into the fluid at the rearward end of the hand piece 300. If the electric stimuli are imparted to the tissue via the fluid, the needle 340 may be electrically insulated to minimize any drain or disbursement of the electric charge through the sidewalls of the needle.

As shown in FIG. 2, the electrical stimulation element is connected with an electric stimuli generator 335, which is an electrical source operable to provide an electrical charge or pulse to the stimulation element. The stimuli generator may be incorporated into the drive unit 50 as shown in FIG. 2. In such an arrangement the stimuli generator 335 is connected with the CPU of the drive unit so that the CPU provides electric signals to control the operation of the stimuli generator. Alternatively, the stimuli generator may be a separate element having a separate power source and separate control.

The system may also include a user operable input mechanism, which allows the operator to provide an input signal for controlling the system. The input mechanism may be any of a variety of devices, such as a handheld or foot operated control that provides a means for the operator to start, stop, and change the flow-rate from a single flow-rate to a second or third distinct pre-set flow rate. Alternatively, the input element may be a button, touchscreen, mouse, keyboard or a microphone for providing input commands audibly. Additionally, the system may include a plurality of input mechanisms to allow the operator to input a variety of inputs for various stages of a procedure. For example, the system may include a first input mechanism, such as a foot pedal that controls the flow of fluid through the device. Actuating the foot pedal switch (i.e. depressing the switch) sends a signal to the CPU of the drive unit, which in turn sends a signal to the motor to drive the motor so that fluid flows from the syringe to the needle 340 as long as the pedal is actuated. Alternatively, actuating the foot pedal a first time may operate a start signal to start the fluid flow and the fluid may continue to flow until the operator actuates the foot pedal again. In this way, the second actuation operates as a stop signal to discontinue the fluid flow. Additionally, the system may include a second input mechanism, such as a touch screen, so that once an electronic simulation is applied to a patient the operator may input an indication of whether or not muscle twitch was detected or whether a sensation is noticed by the patient. Further still, the primary or secondary input mechanism may be a control button, such as button 325 on the hand piece. Actuating the control button 325 may send a signal to the CPU to provide a response input during a procedure.

Calculation of Fluid Pressure at the Exit of the Needle

As discussed above, the fluid pressure is used to control operation of the system 5. For instance, system may provide a signal to the operator when the fluid pressure exceeds a threshold, thereby indicating that the needle may be located intra-fascicularly. There are several methodologies for calculating the fluid pressure at the exit of the needle.

A pressure sensor may detect the fluid pressure in the injection assembly 100. For example, as discussed above the pressure sensor may be an in-line pressure sensor, such as that available by Merit Medical part #0001. Alternatively, a pressure sensor internal to the drive unit 50 may detect the fluid pressure between the syringe 18 and the tubing set 22. Another alternative is using a thumb-pad force sensor to detect the force driving the plunger to calculate the pressure within the syringe. A command signal from the pressure sensor sends data of pressure to the CPU for calculation to determine the exit-pressure. Exit-pressure is calculated by a mathematical formula that subtracts the head-pressure of each of the components proximal to the point of pressure measurements. In addition, a calculated value is provided related to a counter head-pressure that is correlated to specific pace (i.e., rate) of forward movement of a needle through bodily tissues. Thus, a pressure value is input and a calculated pressure value is calculated by taking into account all the anticipated resistances of the system to calculate a final unbiased exit-pressure value. The CPU of the drive-unit calculates the values on the input and preset values available within the software. The final calculated exit-pressure value is used to control the CPU and is used to control the motor that controls the flow of fluid from the syringe 18.

A counter head-pressure may be subtracted from the pressure measurement to determine the final value of the fluid pressure. The counter head-pressure varies in response to the rate of insertion and the counter-head pressure is subtracted from the measured fluid pressure when calculating the fluid exit pressure. For instance, the following values represent the counter-head pressure values for a variety of insertion rates.

| Rate of Forward Movement PACE mm/sec | Counter-Head Pressure |
|---|---|
| 0.10 | 1.25 mm/Hg |
| 0.50 | 6.25 mm/Hg |
| 1.00 | 12.50 mm/Hg |
| 1.50 | 18.75 mm/Hg |
| 2.00 | 25.00 mm/Hg |
| 2.50 | 31.25 mm/Hg |
| 3.00 | 37.50 mm/Hg |
| 3.50 | 43.75 mm/Hg |
| 4.00 | 50.00 mm/Hg |
| 5.00 | 62.50 mm/Hg |
| 6.00 | 75.00 mm/Hg |
| 7.00 | 87.50 mm/Hg |
| 8.00 | 100.00 mm/Hg |
| 9.00 | 112.50 mm/Hg |
| 10.00 | 125.00 mm/Hg |
| 20.00 | 2500 mm/Hg |

Since the rate of insertion significantly affects the counter-head pressure, it is desirable to control the rate of insertion of the needle. Accordingly, the handset 300 may be designed to aid the user in inserting the needle in a controlled and known insertion rate. In the present instance, the hand-piece 300 is re-useable. However, it should be understood that features of the hand-piece can be utilized in a disposable needle assembly.

Referring to FIG. 3, the hand-piece 300 includes a hollow housing 310 and an elongated hollow needle 340 projecting forwardly from the housing. A connector 332 is provided for connecting the hand-piece with the fluid line 22 of the injection assembly 10. Specifically, the connector 332 provides a fluid-tight seal for connecting the hand-piece 300 at the rearward end of the housing to facilitate connection of the hand-piece with the fluid in the syringe. The fluid flows to the hand-piece and out through the needle 340.

The needle 340 includes a plurality of markings 344 along the length of the needle. In particular, the markings include a plurality of lines transverse the axis of the needle. The markings 344 are spaced apart from one another a known distance. More specifically, each marking 344 is spaced apart from the adjacent marking by a uniform distance. The markings preferably extend along at least a substantial portion of the length of the needle. In the present instance, the markings extend from the tip 342 of the needle 340 to the connection point between the housing 310 and the needle. The increments on the surface of the needle may be a laser etching, alternating colors or engravings on the surfaces of the needle at defined distance, such as 1.0 cm increments as an example.

The hand-piece 300 may further include an indicator light 215 configured to provide the operator with regular prompts. The indicator light 315 may be an LED or other light element that flashes at a predetermined frequency based on the intended rate of insertion. Specifically, prior to commencing a procedure, the operator enters various data regarding the procedure and based on the data entered by the operator an insertion rate is determined for the procedure. Based on the insertion rate, the frequency of the blinking indicator 315 is determined. As discussed further below, the indicator light operates similar to a metronome providing a constant pacing element for monitoring the rate of insertion of the needle to improve the accuracy and consistency of the insertion rate of the needle.

The hand-piece further includes an audible indicator 320 such as a piezoelectric audio indicator for providing an audible signal, including, but not limited to a buzz, tone or chime. The audible indicator 320 operates similar to the indicator light 315 by providing a regular tone that can be used to pace the insertion rate of the needle 24.

Additionally, a control button 325 may be provided for the hand-piece. The control button 325 may operate as an on/off button. However, the control button may also be operable to enter various control commands. For instance, the control button 325 may be operable to over-ride one or more operations of the drive unit 50 as discussed further below.

Finally, the hand-piece 300 may also include an output mechanism, such as a display screen for displaying various information, such as the frequency of the indicator light 315 and/or audible indicator 320. Additionally, the display may show additional information, such as real-time pressure values, or alerts "Proceed", "Reposition", "Inject", Flow-rate 1, Flow-rate 2, Low-Speed, High-Speed, "Aspirating".

As described above, the hand set includes both a visual and audible indicator 315, 320. It should be understood that the hand-piece does not need to include both an audible and a visual indicator; it could include just a single indicator. Further still, although a visual and audible indicator are described, a variety of alternate indicators could be used instead, such as a vibration element that provides regular vibration indicator signals.

The defined audible/visual cadence directs the operator to advance the needle forward a defined increment based on the markings 344 on the needle. The forward movement of the specific increment is referenced upon the penetration of the surface of the needle into the surface of the skin, dermis or body part the needle is penetrating. A rate of 1.0 mm/sec to 20 mm/sec is provided as a range of movement of the needle. In particular, the rate of advancement may be 2.0 mm-10 mm/sec. More specifically, the rate of advancement may be 3.0-7.0 mm/sec. The precise rate of movement is achieved by coordinating the audible or visual cadence to the movement of the needle markings that penetrates the surface and is noted by the visual markings on the surface of the needle at specific distances. The marked needle is then advanced one increment thru the surface of the tissue per "beep" and/or "blink".

The rate of audible and/or visual cues is pre-set in the CPU and activated upon fluid flow. It is understood that any rate of movement coordinated incremental movement of a needle displaying markings may be utilized depending on the application. This forward rate of movement selected from the pre-set values will enter a corresponding counter-head pressure value that will be subtracted from the calculation in determining an objective tissue pressure value.

An example of an operational rate is the operator advancing the needle 3.0 mm for each beep sound and visual "blinking" of the LED to provide coordination of a precise needle advancement rate. This design enables a precise rate of needle advancement to be maintained. Additionally, while the needle is being advanced a continuous flow of fluid from the needle is provided and real-time, continuous pressure monitoring is provided.

As noted above, the hand-piece 300 may include a control button. The control button may be utilized when the needle is not being advanced. In such an instance, pressing the button operates to provide a control signal to the drive unit 50 so that a counter-head pressure value will not be subtracted from the calculation of the exit-pressure (since the needle is not being advanced there is zero, or essentially zero, counter-head pressure). It is understood that the button or control on the hand-piece 300 may also be activated to correspond with the forward movements in which the counter head-pressure is subtracted from the calculation of the head-pressure therefore providing a means to distinguish between when the needle is being advanced and when it is remaining stationary within the tissues. In this way, actuation of the button 325 during periods of minimal to zero needle insertion promotes accuracy of the exit-pressure values within the tissues during the procedure. In addition to the switch or control button discussed above, the hand-piece may include a second button or control element in which backward movements would add an additional head-pressure value to compensate for the backward movement which causes a decrease in exit-pressure values when moving a needle backward through the tissues.

In the description above, the hand-piece incorporates a visual or audible indicator 215, 220 to pace the rate of insertion of the needle. Although the indicator(s) may be provided on the hand piece, a separate element such as a light on the drive unit 50 can be used to provide the visual signals for pacing the rate of needle insertion. Alternatively, the visual signal may be projected adjacent the needle tip at a constant and defined rate or frequency similar to how the indicator light 315 blinks. Therefore, the needle can be used separately from the rest of the features of the hand-piece. Specifically, a needle with markings for guiding the rate of insertion can be used with a typical injection assembly, such as injection assembly 10 described above. In such an embodiment, the signal generator will provide the visual cues for guiding the rate of insertion of the needle.

Method of Operation

An exemplary method for administering an epidural injection using the system described above will now be described. It should be understood that the present system is not limited to use in peripheral nerve block procedures. Accordingly, it should be understood that the principles and methods described below may be readily adapted for injections into tissues and anatomical areas in a variety of applications and procedures.

The system may be used to detect whether the needle is positioned within the fascicle (i.e. positioned intra-fascicularly). The system makes the determination based on a combination of several variables. First, if the needle has pierced the endoneurium the fluid pressure will be quite high because the axons are tightly packed within the endoneurium. Additionally, if the needle has pierced the endoneurium the operator is likely to observe a noticeable response to an electrical stimulation applied to the patient at or adjacent the needle tip. Therefore, if the operator notices a high fluid pressure and then applies an electrical stimulation and notices a response, it is likely that the needle is positioned intra-fascicularly and therefore should be re-positioned. Therefore, the system may operate as follows.

Figure 4:
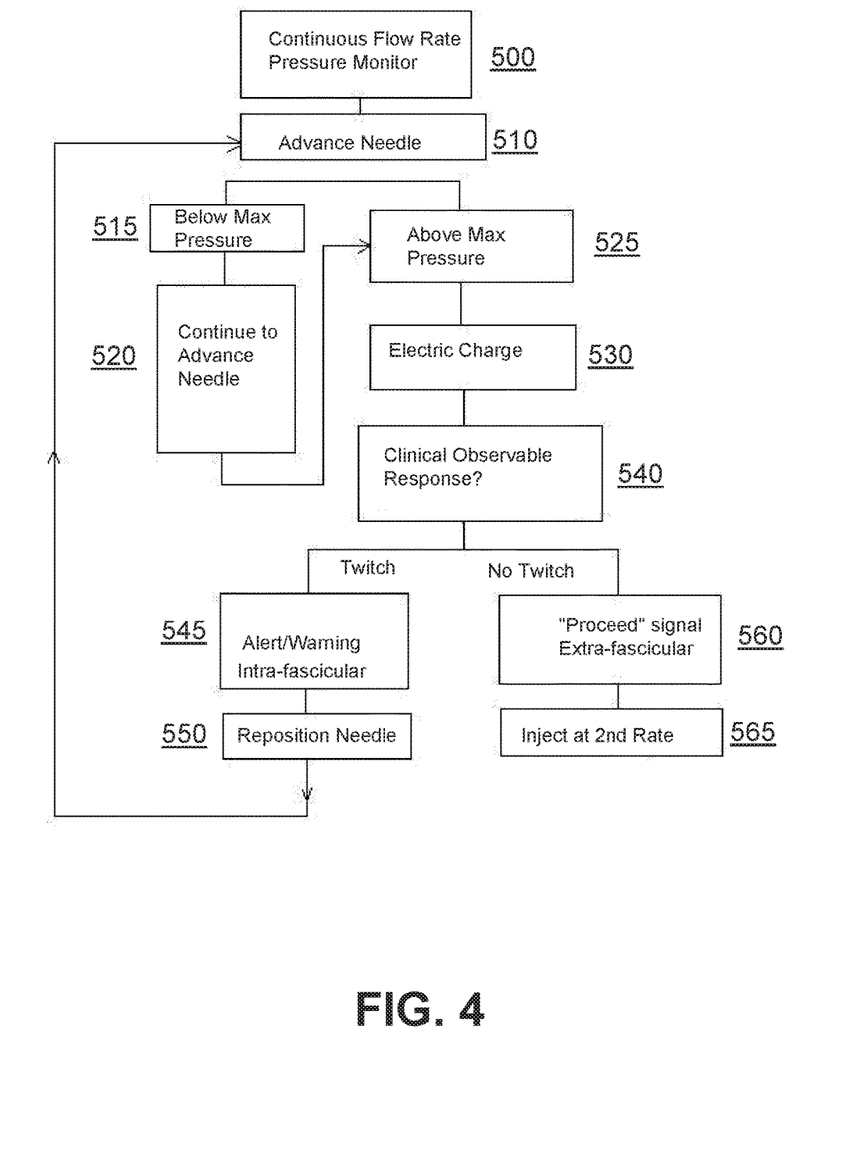
FIG. 4 is a flow chart of a method for injecting fluid.

Referring to FIG. 4, at step 500 the operator selects the procedural parameters, such as the upper threshold and/or the fluid flow rate and/or the rate of needle advancement. For example, the operator may set an upper threshold pressure, such as 300 mm/Hg. Alternatively, the upper threshold may be pre-set in the system when the operator selects the type of procedure for which the system is to be used. Similarly, the operator may select the fluid flow rate through the needle or the flow rate may be set automatically when the operator selects the type of procedure. Additionally, the operator may select the duration of the electrical nerve stimulation when it is applied. Once the procedural parameters are selected, the operator provides an indication that the procedure is to start. For instance, the operator may press a start button on the drive unit.

At step 510 the operator advances the needle into the patient. As discussed above, the needle may be advanced at any of a variety of insertion rates, such as 3 to 10 mm/sec. Preferably, the needle is inserted at a substantially constant rate. Accordingly, at step 510, the operator may insert the needle at a constant rate being guided by the indicator 315 as described above.

At step 515 as the operator advances the needle, the system continuously determines the feedback pressure at the needle and provides feedback either visually or audibly regarding the determined pressure. The visual signal varies as the determined pressure varies.

At step 520 the operator continues to advance the needle as long as the system does not provide a signal indicating that the fluid pressure has exceeded the upper limit.

At step 525 the fluid pressure exceeds the upper threshold so the system provides a warning signal in the form of an audible, visual and/or tactile signal. In response to the signal indicating that the fluid pressure exceeded the upper threshold, the operator stops advancing the needle. Additionally, the drive unit may stop the motor to stop the flow of fluid to the needle.

At step 530 an electrical nerve stimulation signal is applied at or adjacent to the tip of the needle 340. For instance, as described above, an electrical nerve stimulation can be applied to a conductive element positioned adjacent the needle tip. The electric nerve stimulation may be provided automatically by the system in response to the fluid pressure exceeding the upper threshold. For instance, one the fluid pressure exceeds the upper threshold the system provides a signal to the operator. Additionally, at that point or after a short delay, such as 1-3 seconds, the system may provide the electrical nerve stimulation. Alternatively, the operator may apply the electric stimuli by providing an input prompt, such as pressing a button or providing a verbal command. In response to the operator's prompt, the electric nerve stimulation is applied to the patient. In other words, when the fluid pressure exceeds the upper threshold the system prompts the operator to apply the electric charge and in response to the signal the operator applies the electric charge.

At step 540 the operator monitors the patient to detect any clinically observable response, such as a muscle twitch. The operator then provides an input to the system indicative of whether an observable response was detected or not. For instance, the operator may press a first button if the operator noticed a twitch or the operator may press a second button if the operator did not notice a twitch. If the operator noticed an observable response then method proceeds to step 545. If the operator did not notice an observable response then the method proceeds to step 560.

At step 560 the system provides an alert warning to the operator. The alert may be visual, audible and/or tactile. The warning warns the operator that the needle may be positioned intra-fascicularly. For example, the system may provide an audible warning sound, such as the word "warning", while also providing a flashing light on the hand piece.

At step 550 the operator withdraws the needle and repositions the needle in an attempt to place the needle in the target area without piercing the perineurium. In this way, the method re-starts at step 510.

If no observable response it detected at step 540, the method proceeds to step 560. At step 560 the system provides a signal to the operator indicating that the needle is properly located for an injection (i.e. the needle tip is located extra-fascicularly). For example, the drive unit 50 may provide an audible signal such as announcing the word "proceed" or providing a visual signal, such as the word "proceed" on the display screen of the drive unit or the hand piece.

At step 565 the flow rate of fluid is increased to a second rate that is higher than the first rate. The operator may inject a preliminary amount that may be observable so that the operator may detect that the needle is properly placed. Once placement is verified, the operator may inject a bolus of fluid to anesthetize the patient. Alternatively, the operator may inject the bolus of fluid without first injecting an amount to verify the needle placement. Either way, a quantity of fluid is injected at step 565 at a higher rate than the previous low flow rate. Alternatively, in response to an indication that the upper pressure limit was exceeded and an indication that no response was observed in response to the electric nerve stimulation, the drive unit may automatically increase the flow rate, such as by increasing the speed of the motor Another feature of the current device and methodology is the objective nature of pressure measured by a computer-controlled drug delivery device that is monitored during all phases of the injection process. The clinician, therefore, no longer relies on the subjective nature of a "feel" but rather is provided with objective information of absolute values while performing each phase of this critical technique. Each phase of the technique is improved by the ability to objectively monitor the pressure on a continuous basis.

It should be understood that the example of 300 mm/Hg as the maximum pre-set pressure for stoppage of fluid flow is an example and that either a lower or higher pre-set pressure may be selected at the discretion of the clinician. The techniques described herein are equally applicable to human and animal tissues.

It will be recognized by those skilled in the art that changes or modifications may be made to the above-described embodiments without departing from the broad inventive concepts of the invention. For instance, in the foregoing description, the system is described in the context of providing fluid infusion. However, it should be understood that the system may be used for placement of a needle to aspirate fluid-filled tissue. It should therefore be understood that this invention is not limited to the particular embodiments described herein, but is intended to include all changes and modifications that are within the scope and spirit of the invention as set forth in the claims.

What is claimed is:

1. An apparatus for administering fluid into an anatomic space, comprising:
    an injection system for controlling a flow of fluid from a fluid reservoir to a needle, wherein the needle is configured for subcutaneous insertion into a mammalian subject;
    a sensor for detecting a characteristic indicative of the fluid pressure in the needle, wherein the sensor is configured to continuously to detect the characteristic as the needle is inserted into the subject; and
    an electric nerve stimulation element for providing an electric nerve stimulation at or adjacent to a tip of the needle;
    wherein the electric nerve stimulation element provides electric nerve stimulation to a patient after the sensor detects a characteristic of the fluid pressure indicative of the fluid pressure exceeding an upper threshold.

2. The apparatus of claim 1 wherein the system includes an indicator operable to provide an audible, visual or tactile signal.

3. The apparatus of claim 2 wherein the indicator is operable to provide a signal when the fluid pressure exceeds the upper threshold.

4. The apparatus of claim 2 comprising an input element configured to provide a mechanism for an operator to input whether a clinically observable response was observed in response to the electric nerve stimulation.

5. The apparatus of claim 4 wherein the indicator is operable to provide a signal indicative of the needle being in an appropriate position for an injection, wherein the indicator is configured to provide the signal in response to a signal from the input element indicative of no clinically observable response being observed.

6. The apparatus of claim 1 wherein the injection system includes a fluid reservoir and an elongated flexible tube, wherein a first end of the flexible tube is connected with the fluid reservoir and a second end of the flexible tube is connected with the needle.

7. The apparatus of claim 6 wherein the sensor is located in-line between the fluid reservoir and the needle so that the sensor detects the fluid pressure in-line with the flow of fluid between the reservoir and the needle.

8. The apparatus of claim 1 wherein the injection system comprises a microprocessor for controlling the rate of fluid flowing from the fluid reservoir.

9. A method for providing a peripheral nerve block to a patient, comprising the steps of:
    inserting a needle into a patient;
    providing a flow of fluid through the needle while the needle is in the patient;
    monitoring the fluid pressure in the needle while the needle is in the patient;
    providing a human perceptible signal indicative of the fluid pressure exceeding an upper limit; and
    providing an electric nerve stimulation at or adjacent to a tip of the needle in response to the signal.

10. The method of claim 9 comprising the step of monitoring the patient to detect a response to the electric nerve stimulation.

11. The method of claim 10 comprising the step of providing a first signal if a response to the electric nerve stimulation is detected or providing a second signal if no response to the electric nerve stimulation is detected.

12. The method of claim 11 comprising the step of re-positioning the needle in response to the first signal.

13. The method of claim 12 comprising the step of injecting a bolus of fluid in response to the second signal.

14. A system for providing a peripheral nerve block to a patient, comprising:

a needle having a sharpened tip;

a fluid pump providing a flow of fluid to the needle, wherein the fluid pump comprises a microprocessor for controlling the flow of fluid to the needle;

a sensor for detecting the fluid pressure in the needle;

a conductive element for providing an electric nerve stimulation at the tip of the needle; and an output element configured to provide a human perceptible signal wherein in response to a signal indicative of the fluid pressure exceeding an upper limit the output element provides an alert signal to alert the operator to discontinue insertion of the needle;

wherein the conductive element is configured to provide an electric nerve stimulation at or adjacent to the tip of the needle after the sensor detects a fluid pressure exceeding the upper limit.

15. The system of claim 14 comprising an input element configured to allow the operator to indicate whether a clinically observable response was observed in response to the electric nerve stimulation.

16. The system of claim 15 wherein the output element is configured to provide a second alert signal in response to a signal from the input element indicating that a response was observed in response to the electric nerve stimulation.

17. The system of claim 16 wherein the output element is configured to provide a third alert signal in response to a signal from the input element indicating that no response was observed in response to the electric nerve stimulation.

18. The system of claim 14 wherein the fluid reservoir comprises a syringe having a plunger and the injection system comprises a control mechanism for automatically advancing the plunger to expel fluid from the syringe.

19. The system of claim 14 wherein the sensor comprises a pressure transducer.

20. The system of claim 19 wherein the sensor detects fluid pressure and the pump controls the flow of fluid in response to the detected fluid pressure.

* * * * *